United States Patent

Kajiyama et al.

Patent Number: 5,965,769
Date of Patent: Oct. 12, 1999

[54] METHOD FOR HEAT RECOVERY AND UTILIZATION BY USE OF CHEMICAL ENERGY OF SYNTHESIS AND DECOMPOSITION OF METHYL FORMATE

[75] Inventors: Shiro Kajiyama, Tokyo; Futoshi Ikoma, Niigata; Atsushi Okamoto, Niigata; Mikio Yoneoka, Niigata; Shuji Ebata, Niigata; Kenji Nakamura, Niigata, all of Japan

[73] Assignee: Mitsubish Gas Chemical Company, Inc., Tokyo, Japan

[21] Appl. No.: 09/004,101

[22] Filed: Jan. 7, 1998

[30] Foreign Application Priority Data

Jan. 8, 1997 [JP] Japan .................................. 9-001533
Jan. 8, 1997 [JP] Japan .................................. 9-001534
Jan. 17, 1997 [JP] Japan .................................. 9-006791

[51] Int. Cl.$^6$ .......................... C07C 67/36; C01B 31/18
[52] U.S. Cl. ....................... 560/232; 423/418.2; 423/490; 423/622; 165/104.12
[58] Field of Search ...................... 560/232; 423/418.2, 423/490, 622; 165/104.12

[56] References Cited

U.S. PATENT DOCUMENTS 3,812,210  5/1974  Higdon et al. .

FOREIGN PATENT DOCUMENTS 1006533  3/1977  Canada .
0057090  8/1982  European Pat. Off. .
2198925  5/1974  France .
 767225  3/1952  Germany .
09042779  2/1997  Japan .

Primary Examiner—Samuel Barts
Assistant Examiner—Rosalynd Keys
Attorney, Agent, or Firm—Antonelli, Terry, Stout & Kraus, LLP

[57] ABSTRACT

There are herein disclosed a method for heat recovery and heat utilization by the use of chemical energy which comprises the steps of doing the heat recovery by the following formula (I), and doing the heat utilization by the following formula (I'):

$$HCOOCH_3 \rightarrow CH_3OH + CO \qquad (I)$$

$$CH_3OH + CO \rightarrow HCOOCH_3 \qquad (I')$$

the reaction of the formula (I') being carried out in the presence of an alkali fluoride and zinc oxide. According to the present invention, steam or hot water can be generated at a high temperature of 100° C. or more by the use of a factory waste heat or a river water at a low temperature of 100° C. or less as a heat source from which heat has scarcely been utilized so far, and the thus generated steam or hot water can effectively be used as a heat source or be used in an air conditioner. The catalyst which comprises the alkali fluoride and zinc oxide is used for preparing methyl formate or CO gas according to the formula (I) or (I').

7 Claims, 1 Drawing Sheet

METHOD FOR HEAT RECOVERY AND UTILIZATION BY USE OF CHEMICAL ENERGY OF SYNTHESIS AND DECOMPOSITION OF METHYL FORMATE

BACKGROUND OF THE INVENTION

1. Field of the Invention

The present invention relates to a method for utilizing the heat of a low-temperature heat source such as a factory waste heat or a river water by the use of the chemical energy of a synthesis and decomposition reaction system of methyl formate, a method for preparing methyl formate and carbon monoxide, and a catalyst for a liquid phase reaction.

2. Description of the Related Art

Heretofore, for the recovery, transportation and utilization of heat energy, a technique of using water vapor or hot water has prevalently been employed. The application of this technique, however, has largely been restricted from the viewpoints of a heat loss and a facility cost, and hence, the recovery of the low-temperature waste heat has been limited.

That is to say, in various industrial facilities of a large energy consumption type such as power plants and iron works, saving energy has been advanced of late, and most of the waste energy has been recovered. However, the low-temperature waste heat of 200–300° C. or less has been discarded owing to no means for properly utilizing such a waste heat in the self-facilities, so that a large cooling load has often been required.

In recent years, as a method for effectively recovering the low-temperature waste heat to utilize the waste heat for local air-conditioning, hot-water supply and the like, it has been investigated that the heat energy is converted into chemical energy to accomplish the heat recovery and heat utilization.

In this method, although the conversion between the heat energy and the chemical energy is necessary on a heat recovery side and a heat utilization side, transportation of heat energy for a long distance and storage of heat energy are possible, and the heat loss does not occur during the transportation and the storage. In addition, an efficiency of the heat transportation per unit volume in the above method is high. So the above method is also considered to be advantage from the viewpoint of the facility cost.

As an effective conversion system between the heat energy and the chemical energy, there has been suggested a method in which a methanol decomposition reaction of the formula (i) and a methanol synthesis reaction of the formula (i') are used:

In this method, since the methanol decomposition reaction of the formula (i) is an endothermic reaction, the waste heat can be recovered by the use of the reaction of the formula (i), and obtained CO and 2H$_2$ can be transported. In a heat utilization area, the supply of the heat energy can be carried by the exothermic reaction of the formula (i'). Methanol produced by the formula (i') can be circulated to a heat recovery area and is reused therein.

In the conversion system using the formulae (i) and (i'), inexpensive and easily treatable methanol is used and the reaction can easily be carried out, and hence this conversion system is considered to be an effective energy conversion system. However, this kind of system has the following problems.

(1) The heat recovery is restricted by the lower limit temperature of the reaction of the formula (i), however, from the practical viewpoints of a reaction rate and the like, the lower limit temperature for the heat recovery is about 200° C. So it is impossible to recover the heat in a low-temperature range of 200–100° C. to nearly ordinary temperature which are considered to be the most suitable range for the waste heat recovery.

(2) In order to effectively do the heat recovery, it is necessary to decrease the reaction temperature of the formula (i) as low as possible, however, with the decrease in the reaction temperature, the equilibrium relation of the formula (i) becomes noticeably disadvantageous to a methanol decomposition side.

(3) In view of the heat utilization, it is advantageous to carry out the reaction of the formula (i') at a high temperature, however, with the rise in the reaction temperature, the equilibrium relation of the reaction of the formula (i') becomes noticeably disadvantageous to the synthetic reaction of methanol. Furthermore, in order to improve the equilibrium relation, the synthetic reaction of methanol is to be carried out under a high pressure, but the use of the high pressure deteriorates a heat utilization efficiency in view of a device cost, an operation cost and the like. Accordingly, the improvement of the reaction temperature and the pressure characteristics has been desired.

The present inventors have found that the recovery and the utilization of the waste heat can extremely advantageously be done by using, as the above conversion system of the heat energy into the chemical energy, a system of using methyl formate in place of methanol in the above process, i.e., a system including the decomposition of methyl formate into methanol and carbon monoxide and the synthesis of methyl formate from methanol and carbon monoxide represented by the following formulae, and the present inventors have already submitted a patent application (Japanese Patent Application Laid-open No. 42779/1997):

The method for obtaining carbon monoxide by decomposing methyl formate in accordance with the above formula (I) is noticed as a technique of easily obtaining carbon monoxide at a low temperature without using expensive facilities, because methyl formate can be obtained at a low cost from methanol as a main material in a C1 chemical industry and can be transported in the state of a liquid.

As the methods for obtaining carbon monoxide by decomposing methyl formate, there are known (1) a method which comprises thermally decomposing a gaseous phase at a temperature of 200 to 500° C. by the use of a solid catalyst on which an oxide of an alkaline earth metal is supported (U.S. Pat. No. 3,812,210), (2) a method which comprises thermally decomposing a gaseous phase at a temperature of 200 to 550° C. by the use of active carbon as a catalyst (Japanese Patent Application Laid-open No. 36609/1977), and (3) a method which comprises thermally decomposing a liquid phase of methyl formate coexisting with methanol at a temperature of 35 to 200° C. under a pressure of 17.2 MPa or less by the use of sodium methylate as a catalyst (U.S. Pat. No. 3,716,619).

In the methods (1) and (2), the thermal decomposition is carried out at a temperature of 250° C. or more in the gaseous phase, and latent heat for vaporization is required. Therefore, these methods are disadvantageous from the viewpoint of heat energy, and a large amount of impurities is secondarily produced, so that the selectivity of carbon monoxide is low. The above method (3) is excellent in that the reaction conditions of the liquid phase are mild, but it has drawbacks caused by a fact that sodium methylate is strongly basic. That is to say, impurities such as sodium hydroxide and sodium formate are secondarily produced owing to water during the reaction, which causes the catalyst loss, and some insoluble salts also precipitate in the reaction system, which brings about an operation trouble of an apparatus. In addition, during the use of the catalyst, if sodium methylate comes in contact with carbon dioxide or water, the catalyst is deactivated, and its regeneration is not easy. Moreover, since sodium methylate has a very strong irritation to a skin, much attention is required for its handling.

Methyl formate which is prepared by the formula (I') can effectively be utilized as a synthesis material of formic acid, formamide, various carboxylic esters and organic compounds, a solvent or the like, and hence, it is an industrially important organic chemical material.

As the preparation methods of methyl formate, there are known an esterification of formic acid with methanol, a dimerization of formaldehyde, an oxidation of methanol, a direct synthesis from hydrogen and carbon monoxide, a carbonylation of methanol with carbon monoxide, a dehydrogenation of methanol and the like. Among them, the methods which have been put to practical use on an industrial scale include the dehydrogenation method of methanol, and the carbonylation method of methanol which has been used for long years.

The dehydrogenation method of methanol is a novel method which has been put to practical use in recent years, and the development of catalysts having a high selectivity (e.g., Japanese Patent Application Laid-open Nos. 151047/1991 and 163444/1983) permits its practical utilization ["Chemistry and Industry", Vol. 18, p. 1134–1136 (1988)].

The carbonylation method of methanol by the formula (I') has been used for long years in Europe and America, and it is known as the main preparation method of methyl formate even at present. As catalysts to be used, there are known strongly basic catalysts such as metal alkoxides and DBU (diazabicycloundecene) as well as transition metal carbonyl compounds.

As the metal alkoxide catalyst for the carbonylation method, an alkoxide of an alkali metal is used, and a reaction is carried out at a temperature of 50 to 70° C. under a pressure of 1 to 4 MPa [Journal of Molecular Catalysis, Vol. 18, p. 215–222 (1983)]. In the case that the metal alkoxide catalyst is used, water and carbon dioxide in methanol and carbon monoxide which are the raw materials function as catalyst poisons to deactivate and consume the catalyst. Therefore, it is necessary to decrease the amounts of water and carbon dioxide to the utmost, and hence a raw material purification system becomes an important step. Hydrogen present in carbon monoxide gas has not any influence on the reaction.

In the method using the metal alkoxide, the selectivity of methyl formate is high, and this method has actually been employed on an industrial scale. In order to advance the reaction more advantageously, many suggestions regarding reaction methods, structures of reactors, processes and the like have been given.

In the method using a strongly basic catalyst such as DBU, for example, the reaction is carried out at a temperature of 45 to 200° C. under a pressure of 17.2 to 40.5 MPa in the presence of DBU in a methyl cellosolve solvent [Japanese Chemical Journal (4), p. 457–465 (1977)].

With regard to the metal carbonylation catalyst, a ruthenium hydride carbonium catalyst is considered to be effective for a formate synthesis by the carbonylation of an alcohol ["J. Mol. Catal.", Vol. 45, p. 235–246 (1988)].

In all of the above-mentioned methods, the reaction is carried out in a homogeneous catalyst system, but as a heterogeneous catalyst, a basic ion exchange resin is mentioned in U.S. Pat. No. 4,100,360.

In the above-mentioned carbonylation method of methanol, the metal alkoxide catalyst and the DBU catalyst which are strongly basic are used, and therefore this carbonylation method has the following drawbacks.

Firstly, the catalyst is liable to be affected by impurities in methanol and carbon monoxide gas which are the raw materials, and particularly, water and carbon dioxide react with the catalyst to change into insoluble substances, so that they cannot be separated any more, or salts of formic acid are secondarily produced. Consequently, in addition to the loss of the catalyst, even the operation itself of an apparatus might be impossible. In order to prevent this affection, it is necessary to completely purify methanol and carbon monoxide which are the raw materials, but for such a purification, a complicated process and a large amount of energy are required, which leads to an industrially large load. In addition, if the metal alkoxide comes in contact with $CO_2$ or water during its handling and it deactivates, its regeneration is difficult. Moreover, since the metal alkoxide has a very strong irritation to a skin, much attention is required for the handling.

Furthermore, the basic ion exchange resin has a high initial activity and is excellent as the heterogeneous system catalyst, but its activity deteriorates with time. In addition, owing to a low heat resistance of the basic ion exchange resin, the quality change of the resin is unavoidable.

SUMMARY OF THE INVENTION

An object of the present invention is to provide a conversion system between heat energy and chemical energy in which the decrease in a heat recovery temperature is intended and a heat utilization performance is heightened from the viewpoints of an apparatus cost and an operation cost.

As described above, the present inventors have previously found that when a system of using methyl formate in place of methanol in the above system, i.e., a system including the decomposition of methyl formate into methanol and carbon monoxide and the synthesis of methyl formate from methanol and carbon monoxide represented by the following formulae is used as the conversion system between the heat energy and the chemical energy, the recovery and the utilization of a waste heat can extremely advantageously be carried out:

  $HCOOCH_3 \rightarrow CH_3OH + CO$              (I) (Endothermic reaction)

  $CH_3OH + CO \rightarrow HCOOCH_3$              (I') (Exothermic reaction)

According to this method, a strongly basic ion exchange resin is used as a catalyst for the reaction of the formula (1), whereby methyl formate can be decomposed at a low temperature, and consequently, the heat recovery can effectively be accomplished. However, in the synthesis reaction of methyl formate by the formula (I'), the temperature cannot be raised in consideration of the low heat resistance of the ion exchange resin, so that it is difficult to effectively utilize the heat.

That is to say, if the reaction temperature can be raised in the preparation method of methyl formate by the carbonylation of methanol in accordance the formula (I'), the extremely effective system of the heat recovery and the heat utilization will be established.

The present inventors have investigated on such a waste heat recovery and utilization system as described above, and as a result, it has been found that a catalyst comprising a combination of an alkali fluoride and zinc oxide can exert a high activity in a methyl formate synthesis reaction to permit the production of methyl formate with an extremely high selectivity for a long period of time, and hence a low-temperature heat source can extremely effectively be utilized by this system using this catalyst. In consequence, the present invention has been attained.

That is to say, the present invention is directed to a method for heat recovery and heat utilization by the use of chemical energy which comprises the steps of doing the heat recovery by the following formula (I), and doing the heat utilization in the presence of an alkali fluoride and zinc oxide by the following formula (I'):

In the heat recovery step by the formula (I), a strongly basic ion exchange resin is used.

The novel catalyst comprising the combination of the alkali fluoride and zinc oxide exhibits a high activity in the methyl formate synthesis reaction by the carbonylation method of methanol, and enables the preparation of methyl formate with an extremely high selectivity for a long term. Furthermore, since the catalyst is not strongly basic, methyl formate can industrially advantageously be prepared without the above-mentioned drawbacks.

Moreover, the catalyst comprising the combination of the alkali fluoride and zinc oxide can be used in various liquid phase reactions, and it can exert the high activity and the high selectivity similarly in the preparation of carbon monoxide by a methyl formate decomposition reaction in a liquid phase. In addition, since the alkali fluoride and zinc oxide are not strongly basic, they can easily be handled, so that carbon monoxide can advantageously be prepared on an industrial scale.

DESCRIPTION OF THE PREFERRED EMBODIMENTS

Figure 1:
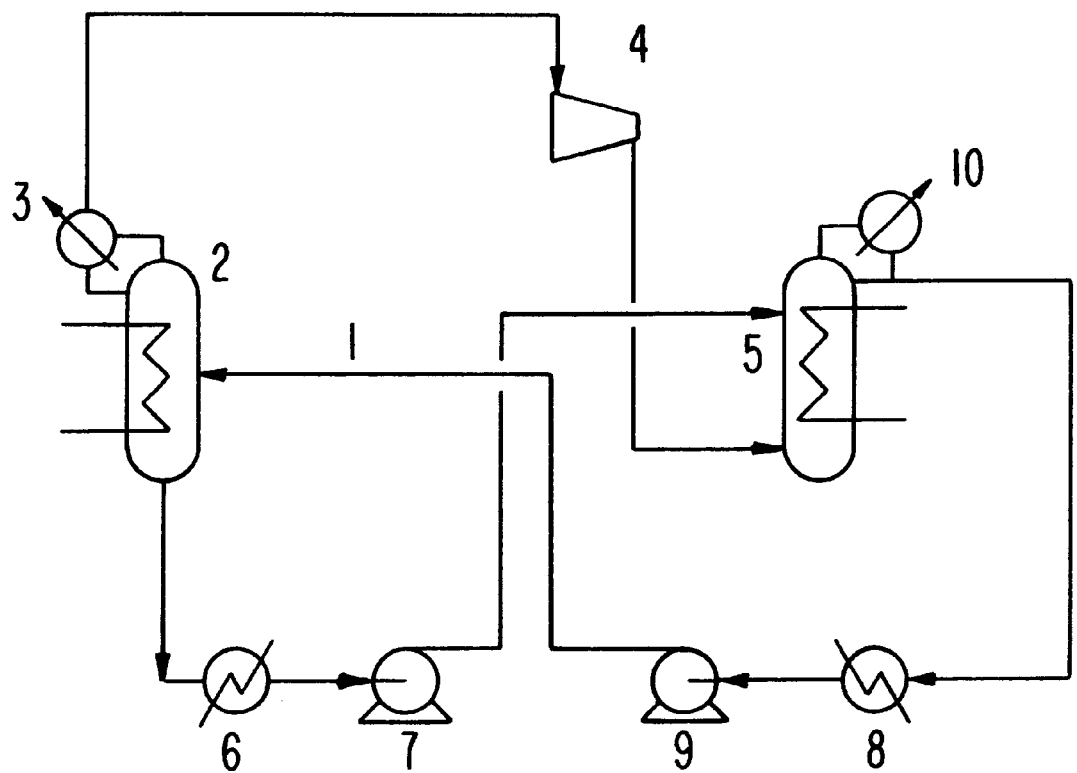
FIG. 1 is a flow chart showing one embodiment of a system of heat recovery and heat utilization used in examples regarding the present invention.

In a method for heat recovery and heat utilization by the use of chemical energy, the decomposition reaction of methyl formate in accordance with the formula (I) can be used in the case of methyl formate alone or under the coexistence of methyl formate and a solvent. Examples of the usable solvent include alcohols such as methanol, ethanol, 1-propanol, 2-propanol, 1-butanol, 2-butanol and 1-pentanol.

A strongly basic anion exchange resin which can be used in the formula (I) is a resin as a parent material having a crosslinking structure into which an anion exchange group is introduced. Examples of the usable parent material of the resin include crosslinked polystrenes of styrene-divinyl benzene series, polyacrylates of acrylic acid series, and heat-resistant aromatic polymers into which an ether group or a carbonyl group is introduced.

In general, as examples of the anion exchange group in the ion exchange resin, there are known amino groups, substituted amino groups and quaternary ammonium groups, but in the strongly basic anion exchange resin which can be used in the present invention, a quaternary ammonium group having a trialkyl-substituted nitrogen atom (—N+$R_3$) and a quaternary ammonium group having a dialkylethanolamine cation such as —N+$(CH_2)_2$.$(C_2H_4OH)$ are suitable. Examples of commercially available products of the strongly basic anion exchange resin for use in the present invention include Amberlist A-26, Dow-X TG-550A, Lewatit M504 and Diaion PA306.

In the case that a solvent is used, a weight ratio of methyl formate to the alcohol is in the range of 1:0–10, preferably 1:0–3. No particular restriction is put on this range of the weight ratio, and it can suitably be selected in view of an amount of the catalyst to be used, reaction conditions and the like.

In the reaction of the formula (I), a reaction temperature and a reaction time can be selected in a wide range in consideration of the weight ratio of methyl formate to the solvent, an amount of the catalyst to be fed and a desired conversion, but as the usual reaction conditions, the reaction temperature is in the range of 0 to 250° C., particularly preferably 20 to 100° C. If the reaction temperature is too low, a practical reaction rate cannot be obtained, and if it is too high, secondary reactions and the deactivation of the catalyst are liable to occur. In addition, a heat quantity to be recovered inconveniently decreases. The reaction time is in the range of 0.1 to 20 hours, particularly preferably 0.2 to 10 hours.

With regard to a reaction pressure in the formula (I), the lower the reaction pressure is, the more advantageous an equilibrium condition is, though the decomposition can be accomplished under a vapor pressure at the decomposition temperature. The reaction pressure is usually in the range of atmospheric pressure to 30 atm, practically preferably atmospheric pressure to 20 atm.

A usual reaction system of the formula (I) may be a fluidized bed, a fixed bed or the like. Furthermore, the decomposition reaction of methyl formate by the formula (I) is preferably carried out in a liquid phase, and the equilibrium reaction can be accelerated by carrying out the reaction in the liquid phase to remove produced CO gas from a reaction system.

The reactions of the formulae (I) and (I') are chemical equilibrium reactions, and in a gaseous phase reaction, restrictions are put on an equilibrium composition. In the liquid phase reaction, however, the produced CO gas is immediately separated from the liquid phase, and hence the liquid phase reaction is advantageous.

If the CO gas and methanol are separated from methyl formate by reaction distillation in order to accelerate the reaction of the formula (I), the chemical equilibrium is advantageous. For example, even if, a one-pass conversion is low, the conversion in the system can be heightened by the utilization of the reaction distillation, and so the employment of the reaction distillation can provide the system having a higher efficiency as compared with a prevalent circulation system.

An alkali fluoride which can be used in the catalyst for the reaction of the formula (I') in the present invention is a fluoride of an element in the group Ia of the periodic table, and examples of the alkali fluoride include sodium fluoride, potassium fluoride and cesium fluoride. Since these alkali fluorides do not react with $CO_2$, they do not deactivate by $CO_2$ in air. Even if the alkali fluoride absorbs moisture, it can be used again after drying at 100° C. or more. Therefore, the handling of the alkali fluoride in the air is possible.

Furthermore, as zinc oxide which can be used in the catalyst for use in the present invention, a commercially available product can directly be used. Alternatively, zinc oxide may be supported on a carrier such as alumina, silica or the like, or a carrier component may be added to zinc oxide by a co-precipitation method or the like and the thus prepared product may be used. It is desirable that zinc oxide does not come in contact with water or $CO_2$ in the air during its handling, but a maximum activity can easily be exerted by subjecting zinc oxide to a pretreatment at 200 to 800° C.

In the method of the present invention, the alkali fluoride and zinc oxide are used at the same time as the catalyst. When the alkali fluoride or zinc oxide is separately used, the activity is extremely low, but when both of them are used together, surprisingly the activity noticeably increases. In addition, the irritation of the alkali fluoride and zinc oxide to a skin is not so strong as that of sodium methylate, and they can easily be handled in an industrial scale.

In the method for preparing methyl formate by the reaction of methanol with carbon monoxide, the alkali fluoride and zinc oxide can be used in combination, and in this case, they can be used in an optional form without any restriction. For example, the alkali fluoride may be supported on zinc oxide, or they may be mixed. A molar ratio of the alkali fluoride to zinc oxide is in the range of 0.05 to 50, preferably 0.1 to 10.

Methanol which is the raw material of the reaction of the formula (I'), prior to its use, is preferably dried with a desiccant or the like to decrease a moisture content in methanol.

Carbon monoxide may contain gases such as hydrogen and nitrogen which are inert to the intended reaction, but since carbon dioxide and water have a bad influence on the reaction, their contents should be decreased to the utmost. Thus, carbon monoxide, prior to its use, is preferably subjected to a gas purification step for the removal of moisture and carbon dioxide.

The catalyst comprising the combination of the alkali fluoride and zinc oxide subjected to such a purification step can stably be used for a long term.

A molar ratio of carbon monoxide to methanol is theoretically 1:1, but there can be employed conditions that carbon monoxide is slightly excessive. Unreacted carbon monoxide separated from a reactor or a reaction tube can circularly be reused through the reaction system.

Furthermore, no particular restriction is put on a molar ratio of methanol to the catalyst, but it is usually in the range of 50:1 to 500:1.

A pressure for the reaction of methanol with carbon monoxide is in the range of 0.5 to 20 MPa, preferably 1 to 10 MPa. A reaction temperature is in the range of 50 to 250° C., preferably 100 to 200° C.

The reaction of the formula (I') is an equilibrium reaction, and produced methyl formate has a lower boiling point than methanol which is the raw material. Therefore, if a reaction distillation system is employed in which methanol is fed to an upper portion of a distillation column and carbon monoxide is fed to a bottom thereof, and produced methyl formate is continuously drawn from the reaction system by distillation to break the equilibrium, methyl formate can easily be obtained with a high conversion.

In the method of the present invention, the reaction can be carried out under a lower pressure as compared with the case of a conventional synthesis and decomposition reaction of methanol, and the reaction of producing methanol from methyl formate is carried out at a lower temperature. Therefore, the method of the present invention is advantageous for the heat recovery at the low temperature. Particularly, by using the strongly basic ion exchange resin as the catalyst in the reaction of the formula (I), a low-temperature heat source at ordinary temperature to 100° C. can be utilized, and hence, the method of the present invention can be applied to a heat pump in which a factory waste heat or a river water is used as the heat source.

Moreover, by carrying out the reaction of the formula (I') by the use of the catalyst comprising the combination of the alkali fluoride and zinc oxide regarding the present invention, steam can be generated at a high temperature of 100° C. or more, and it can effectively be used as a heat source in a factory or be used in an air conditioner.

Consequently, according to the present invention, steam or hot water can be generated at a high temperature of 100° C. or more by the use of a factory waste heat or a river water at a low temperature of 100° C. or less as a heat source from which heat has scarcely been utilized so far, and the thus generated steam or hot water can effectively be used as a heat source or be used in an air conditioner in a factory or at a heat demand area in a city.

In addition, the method of the present invention can be applied to a heat pump, whereby it can be used in an air conditioner or the like in a factory or an office.

Since the method of the present invention is carried out under mild conditions, i.e., a relatively low pressure, a device cost is low, and since the heat recovery and the heat utilization can effectively be carried out by the use of the reaction distillation in the liquid phase reaction, the method of the present invention is extremely excellent as measures of saving energy.

The catalyst comprising the combination of the alkali fluoride and zinc oxide regarding the present invention can exert a high activity in a methyl formate synthesis reaction by the carbonylation method of methanol, whereby methyl formate can be obtained with a high selectivity for a long term. Moreover, since the catalyst is not strongly basic, the use of the catalyst permits the preparation of methyl formate industrially advantageously without the above-mentioned drawbacks.

No particular restriction is put on a reaction process for the preparation of methyl formate by the carbonylation method of methanol, but the reaction process is usually accomplished by mixing the catalyst with methanol of a liquid phase, and then introducing carbon monoxide to the mixture. There can be utilized a batch process in which a tank type reactor having an internal stirring machine is used, or a semi-batch process in which the reaction is carried out while carbon monoxide or methanol which is the raw material is fed.

If methanol containing the dissolved alkali fluoride is used as the raw material in the preparation of methyl formate and if there is employed a procedure in which zinc oxide is stored in a reactor and is afterward separated from a produced liquid, methyl formate can be obtained without being decomposed when taken out by distillation, because a methyl formate decomposition activity is very low in the case that the alkali fluoride alone is used.

For example, there can be utilized a trickle bed system in which a tube reactor is filled with the zinc oxide catalyst, and carbon monoxide and methanol containing the dissolved alkali fluoride are continuously fed in a parallel flow from an upper portion of the reaction tube, or another system in which methanol containing the dissolved alkali fluoride is continuously fed from a lower portion of the reactor, and carbon monoxide is continuously fed in a parallel flow or a counter flow.

A mixture of methanol containing the dissolved alkali fluoride and methyl formate is obtained from the reaction tube, and from this point, a circulation system is also possible in which methyl formate is separated by the distillation and the collected methanol containing the dissolved alkali fluoride is then circulated to feed it together with fresh methanol to the reactor.

Furthermore, this reaction is an equilibrium reaction, and produced methyl formate has a lower boiling point than methanol which is the raw material. Therefore, if a reaction distillation system is employed in which produced methyl formate is continuously drawn out from the reaction system by the distillation to break the equilibrium, methyl formate can easily be obtained with a high conversion.

As described above, the catalyst comprising a combination of the alkali fluoride and zinc oxide regarding the present invention can be used in various liquid phase reactions, and the catalyst can exert a high activity and a high selectivity also in the preparation of carbon monoxide by a methyl formate decomposition reaction in a liquid phase. In addition, since the alkali fluoride and zinc oxide are not strongly basic, they can easily be handled to permit the preparation of carbon monoxide advantageously on an industrial scale.

Methyl formate which is the raw material in the preparation of carbon monoxide can directly be used in an industrial grade as it is, but prior to its use, it is preferable to decrease a moisture content of methyl formate to the utmost by the use of a desiccant or the like. No particular restriction is put on a molar ratio of methyl formate to the catalyst, but it is preferably in the range of 50:1 to 500:1.

A reaction temperature of a methyl formate decomposition in the preparation of carbon monoxide by the use of the catalyst comprising the combination of the alkali fluoride and zinc oxide is in the range of 100° C. to less than a critical temperature of methyl formate, preferably 120° C. to 200° C. With regard to a reaction pressure, it is desirable to use the reaction pressure which is higher than a vapor pressure of methyl formate at the reaction temperature, for the sake of the stable maintenance of the liquid phase in the reactor. A difference between the reaction pressure and a vapor partial pressure of methyl formate can be compensated by an inert gas such as nitrogen, argon or helium and decomposed gases. No particular restriction is put on a reaction system of the methyl formate decomposition, and any system is acceptable, so long as it enables the raw materials to come in contact with the catalyst. Both of a batch system and a flow system are utilizable.

Next, the present invention will be described in more detail in accordance with examples. However, the scope of the present invention should not be limited to these examples at all.

REFERENCE EXAMPLE (Decomposition of methyl formate)

In a 100 ml stainless steel autoclave was placed 10.3 g (0.17 mol) of methyl formate, and 2 ml of a strongly basic anion exchange resin which was previously treated with an 1N aqueous NaOH solution to change into an OH type [Amberlist A-26, made by Rohm & Haas Co., Ltd.] was added thereto, followed by a reaction at 30° C. for 1 hour.

After the contents in the autoclave were cooled to room temperature, a produced gas was drawn from the autoclave, and the used catalyst was separated by filtration and the resulting reaction solution was then analyzed by gas chromatography. As a result, 100% of the produced gas was carbon monoxide, and a decomposition ratio of methyl formate was 30.0%.

EXAMPLES 1 to 6

(Synthesis of methyl formate)

In a 100 ml stainless steel autoclave was placed predetermined amounts of a catalyst and methanol. After the autoclave was sufficiently purged with nitrogen, carbon monoxide was introduced thereinto until a predetermined pressure was reached. The mixture was heated to a predetermined temperature under shaking. After a reaction was carried out for 2 hours under the shaking, the autoclave was cooled in water. A valve of the autoclave was opened to slowly purge an inside gas, and an amount of the gas was metered and a composition of the gas was then analyzed. After the pressure in the autoclave became atmospheric pressure, the contents were taken out, weighed, and then analyzed. The reaction conditions and the results of the respective examples are shown in Table 1.

TABLE 1

|  | Example 1 | Example 2 | Example 3 |
|---|---|---|---|
| Catalyst (g) | KF (0.32 g) ZnO (0.27 g) | KF (0.32 g) ZnO (0.27 g) | KF (0.32 g) ZnO (0.27 g) |
| Methanol (mmol) | 314 | 314 | 314 |
| CO Filling Pressure (MPa) | 4.9 | 4.9 | 4.9 |
| Reaction Temp. (° C.) | 120 | 150 | 180 |
| Yield of Methyl Formate (mol %) | 24.0 | 11.5 | 5.0 |
| Selectivity of Methyl Formate (%) | 9.99 | 9.99 | 9.99 |

| | Example 4 | Example 5 | Example 6 |
|---|---|---|---|
| Catalyst (g) | KF (0.32 g) ZnO (0.03 g) | KF (0.32 g) ZnO (0.27 g) | KF (0.07 g) ZnO (0.33 g) |
| Methanol (mmol) | 312 | 314 | 188 |
| CO Filling Pressure (MPa) | 4.9 | 4.9 | 7.8 |
| Reaction Temp. (° C.) | 120 | 120 | 120 |
| Yield of Methyl Formate (mol %) | 12.8 | 12.0 | 39.9 |
| Selectivity of Methyl Formate (%) | 9.99 | 9.99 | 9.99 |

EXAMPLE 7

(Calculation of heat recovery and heat utilization system)

On the basis of the reference example and the examples described above, the calculation of a heat recovery and a heat utilization system according to the present invention is made. A flow chart used in this example is shown in FIG. 1.

In FIG. 1, methyl formate (100 kg-mol/hr) which is a raw material of the reaction of the formula (I) is fed at 30° C. to a methyl formate decomposition reactor 2 through a flow path 1. The methyl formate decomposition reactor 2 is filled with a strongly basic anion exchange resin used in a distillation reactor in the reference example, and a heat recovery at a low temperature by the reaction at a temperature of 30° C. under a pressure of 20 atm is conducted by an internal heat exchanger (the conversion of methyl formate is 20%). The resulting gas is cooled to 15° C. by a condenser 3 arranged at the top of the methyl formate decomposition reactor 2, and carbon monoxide produced by the decomposition of methyl formate is pressurized by a CO compressor 4, and then forwarded to a methyl formate synthesis reactor 5.

On the other hand, methanol produced by the reaction of the formula (I) in the methyl formate decomposition reactor 2 is cooled to 25° C. by a cooler 6 and then forwarded to the methyl formate synthesis reactor 5 via a methanol feed pump 7. The methyl formate synthesis reactor 5 is also filled with a catalyst used in a distillation reactor in Example 1, and a heat utilization at a high temperature by the reaction of the formula (I') at a temperature of 150° C. under a pressure of 22 atm is conducted by an internal heat exchanger (the conversion of methyl formate is 11.5%). A condenser 10 is disposed at the top of the methyl formate synthesis reactor 5, and the resulting gas is cooled to 149° C., followed by reflux. Produced methyl formate is cooled to 25° C. by a cooler 8, and then forwarded to the methyl formate decomposition reactor 2 via a methyl formate feed pump 9.

In the above-mentioned system, a recovered heat quantity (1) in the methyl formate decomposition reactor according to the reaction of the formula (I) is $0.664 \times 10^6$ kcal/hr (30° C.); a utilized heat quantity (2) in the methyl formate synthesis reactor according to the reaction of the formula (I') is $0.534 \times 10^6$ kcal/hr (150° C.); a cooling heat quantity (3) in the respective condensers and coolers is $0.193 \times 10^6$ kcal/hr; and a required power (4) of a CO compressor 4 and the respective pumps is $0.068 \times 10^6$ kcal/hr on conditions that a power efficiency is 38.2%.

In consequence, a heat transportation efficiency [(2)/{(1)+(3)+(4)}] of this system is 57.7%, and a result coefficient of performance [COP=(2)/(4)] in a heat utilization section is 9.62. Therefore, it is apparent that in this system, the heat transportation efficiency can be achieved at an extremely high level by obtaining a high-temperature heat of 150° C. from a low-temperature heat source of 30° C.

As is apparent from this example, in the method of the heat recovery and the heat utilization according to the present invention, a high-temperature heat of about 150° C. can be obtained from a low-temperature heat source of about 30° C. and such a heat utilization as has not been obtained so far can be accomplished with the extremely high efficiency.

EXAMPLEs 8 to 10

(Preparation of methyl formate)

In Examples 8 and 9, a stainless steel tube type reactor filled with zinc oxide of 10 to 20 mesh was installed in a flow reaction apparatus, and in Example 10, a stainless steel tube type reactor filled with a catalyst of alumina on which 10% of zinc oxide was supported was installed therein. In Example 10, the catalyst was prepared by impregnating an alumina having a particle diameter of 2.3 mm with zinc nitrate, drying and then calcining it. Each reactor was sufficiently purged with nitrogen gas, and it was confirmed that any leakage of gas from the reactor was not present. Next, the pressure in the reactor was raised to 4.9 MPa with carbon monoxide, and the temperature in the reactor was heated up to 120° C. Next, methanol in which 1.0% of dried potassium fluoride was dissolved was fed to the reactor to start a reaction. The experiment was done under conditions that a gas flow rate and a reaction pressure were constant. The resulting reaction product was cooled and then subjected to gas-liquid separation, and the separated liquid product was analyzed. In Example 8, the catalyst held an initial activity even after 500 hours from the start of the reaction.

The reaction conditions and the results are shown in Table 2.

TABLE 2

|  | Example 8 | Example 9 | Example 10 |
|---|---|---|---|
| Catalyst (g) | ZnO (10 ml) | ZnO (10 ml) | ZnO (10%)/$Al_2O_3$ (10 ml) |
| Raw Material | Methanol Containing KF (1.0%) | | |
| LHSV (l/hr) | 0.16 | 0.26 | 0.16 |
| GHSV (l/hr) | 72 | 72 | 72 |
| Reaction Pressure (MPa) | 4.9 | 4.9 | 4.9 |
| Reaction Temp. (° C.) | 120 | 120 | 120 |
| Reaction Time (hr) | 140 | 500 | 46 |
| Yield of Methyl Formate (mol %) | 23.6 | 23.6 | 18.9 |
| Selectivity of Methyl Formate (%) | 99.9 | 99.9 | 99.9 |

EXAMPLE 11

(Preparation of methyl formate)

A stainless steel tube type reactor was filled with 9.7 ml of a CSF (5%)/ZnO catalyst prepared by impregnating zinc oxide of 10 to 20 mesh with an aqueous cesium fluoride solution and installed in a flow reaction apparatus, and a reaction was then carried out in the same manner as in Examples 8 to 10 except that a raw material was methanol and reaction conditions were pressure=4.9 MPa, temperature=180° C., LHSV=0.35/hr and GHSV=36/hr. As a result, a yield of methyl formate was 5.0%, and a selectivity of methyl formate was 98.8%. Thus, the yield of methyl formate at a temperature of 180° C., i.e., 5.0% was close to an equilibrium value.

COMPARATIVE EXAMPLES 1 to 3

Predetermined amounts of a catalyst and methanol were placed in a 100 ml stainless steel autoclave. A lid of the autoclave was closed, and the autoclave was sufficiently purged with nitrogen gas and it was confirmed that any leakage of the nitrogen gas was not present. Next, carbon monoxide was introduced into the autoclave until a predetermined pressure was attained. The mixture was heated to a predetermined temperature under shaking. After a reaction was carried out for 2 hours under the shaking, the autoclave was taken out from a shaking table and then immersed in water to cool it. A valve of the autoclave was opened to slowly purge an inside gas, and an amount of the gas was metered and a composition of the gas was then analyzed. After the pressure in the autoclave became atmospheric pressure, the contents in the autoclave were taken out, weighed, and then analyzed. The reaction conditions and the results of the respective comparative examples are shown in Table 3.

TABLE 3

|  | Comparative Example 1 | Comparative Example 2 | Comparative Example 3 |
|---|---|---|---|
| Catalyst (g) | KCl (0.39 g) + ZnO (0.39 g) | ZnO (0.37 g) | KF (0.32 g) |
| Methanol (mmol) | 313 | 313 | 316 |
| CO Filling Pressure (MPa) | 4.9 | 4.9 | 4.9 |
| Reaction Temp. (° C.) | 120 | 120 | 120 |
| Yield of Methyl Formate (mol %) | 0.6 | 0.3 | 0.7 |
| Selectivity of Methyl Formate (%) | 99.9 | 99.9 | 99.9 |

It is apparent from the results of the above Comparative examples that when the combination of potassium chloride and zinc oxide, potassium fluoride alone or zinc oxide alone is used, a methyl formate synthesis activity is very low, but in the examples regarding the present invention in which the catalyst comprising the combination of the alkali fluoride and zinc oxide is used, the high activity can be exerted to obtain methyl formate with an extremely high selectivity for a long term.

EXAMPLE 12

(Preparation of CO)

In a 100 ml stainless steel autoclave were placed 0.32 g of potassium fluoride, 0.30 9 of zinc oxide and 176 mnmol of methyl formate. The autoclave was sufficiently purged with nitrogen gas, and the mixture was then heated up to 180° C. under shaking. After a reaction was carried out for 2 hours under the shaking, the autoclave was cooled in water. An inside gas in the autoclave was slowly purged, and an amount of the gas was metered and a composition of the gas was then analyzed. After the pressure in the autoclave became atmospheric pressure, the contents in the autoclave were taken out, weighed, and then analyzed. As a result, a yield of carbon monoxide was 30.1%, and a molar ratio of $CO/H_2$ in the produced gas was 99.75/0.25.

EXAMPLE 13

(Preparation of CO)

In a 100 ml stainless steel tank type autoclave equipped with an internal stirring machine were placed 1.2 g of potassium fluoride, 1.6 g of zinc oxide and 833 mmol of methyl formate. The autoclave was sufficiently purged with nitrogen gas so that a nitrogen gas pressure might be 4.9 MPa. Next, the mixture in the autoclave was heated up to 180° C. with stirring. Since a gas is formed with the progress of a reaction, the reaction was carried out for 2 hours while the gas was drawn out so that the pressure in the autoclave might be constant at a level of 4.9 MPa, and the autoclave was then cooled in water to terminate the reaction. A valve of the autoclave was opened to slowly purge an inside gas, and an amount of the gas was metered and a composition of the gas was then analyzed. After the pressure in the autoclave became atmospheric pressure, the contents in the autoclave were taken out, weighed, and then analyzed. As a result, a yield of carbon monoxide was 88.3%, and a molar ratio of $CO/H_2$ in the produced gas was 99.95/0.05.

EXAMPLE 14

(Preparation of CO)

The same procedure as in Example 12 was conducted except that 0.86 g of cesium fluoride, 0.32 g of zinc oxide and 167 mmol of methyl formate were used. As a result, a yield of carbon monoxide was 90.9%, and a molar ratio of $CO/H_2$ in a produced gas was 98.6/1.4.

COMPARATIVE EXAMPLES 4 and 5

(Preparation of CO)

Predetermined amounts of a catalyst and methyl formate were placed in a 100 ml stainless steel autoclave. The autoclave was sufficiently purged with nitrogen gas, and the mixture was heated to 180° C. under shaking. After a reaction was carried out for 2 hours under the shaking, the autoclave was cooled in water to terminate the reaction. A valve of the autoclave was opened to slowly purge an inside gas, and an amount of the gas was metered and a composition of the gas was then analyzed. After the pressure in the autoclave became atmospheric pressure, a lid of the autoclave was opened, and the contents therein were taken out, weighed, and then analyzed. The reaction conditions and the results of the respective comparative examples are shown in Table 4.

TABLE 4

|  | Comparative Example 4 | Comparative Example 5 |
|---|---|---|
| Catalyst | ZnO (0.31 g) | KF (0.32 g) |
| Methyl Formate (mmol) | 172 | 167 |
| Reaction Temp. (° C.) | 180 | 180 |
| Yield of Carbon Monoxide (mol %) | 0.5 | 0.0 |
| Selectivity of Carbon Monoxide (%) | 100 | — |

It is apparent from the results of the above comparative examples that when potassium fluoride or zinc oxide alone is used, a methyl formate decomposition activity is extremely low, but in the examples regarding the present invention in which the catalyst comprising the combination of potassium fluoride and zinc oxide is used, the methyl formate decomposition activity is high.

What is claimed is:

1. A method for heat recovery and heat utilization by the use of chemical energy which comprises the steps of doing the heat recovery by the following formula (I), and doing the heat utilization in the presence of an alkali fluoride and zinc oxide by the following formula (I'):

$$HCOOCH_3 \rightarrow CH_3OH + CO \quad (I)$$

$$CH_3OH + CO \rightarrow HCOOCH_3 \quad (I').$$

2. The method for heat recovery and heat utilization by the use of chemical energy according to claim 1 wherein methanol is fed to a distillation column through its top, and carbon monoxide is fed to the distillation column through its bottom, whereby the reaction of the formula (I') is carried out in reaction distillation.

3. The method for heat recovery and heat utilization by the use of chemical energy according to claim 1 wherein the reaction of the formula (I) is carried out in the presence of a strongly basic anion exchange resin in a liquid phase.

4. The method for heat recovery and heat utilization by the use of chemical energy according to claim 3 wherein methyl formate, CO gas and methanol are separated by reaction distillation.

5. A method for preparing methyl formate which comprises the step of reacting methanol with carbon monoxide in the presence of an alkali fluoride and zinc oxide in a liquid phase.

6. The method for preparing methyl formate according to claim 5 wherein methanol as a raw material containing the dissolved alkali fluoride is reacted with carbon monoxide in the presence of zinc oxide, and after the separation of zinc oxide from the resulting reaction solution, methyl formate is separated by distillation.

7. A method for preparing carbon monoxide which comprises the step of decomposing methyl formate in the presence of an alkali fluoride and zinc oxide in a liquid phase.

* * * * *